United States Patent [19]
Sasahara et al.

[11] Patent Number: 5,640,088
[45] Date of Patent: Jun. 17, 1997

[54] PROCESS FOR MEASURING STRESS OF MAGNETIC MATERIALS, FRP MEMBER WHOSE INTERNAL DAMAGE IS DETECTABLE, AND ADHESIVE LAYER FORMING ADHESIVE MEMBER WHOSE INTERNAL DEFECTION IS DETECTABLE

[75] Inventors: Jun Sasahara; Hajime Goto; Tadahiro Kubota, all of Saitama, Japan

[73] Assignee: Honda Giken Kogyo Kabushki Kaisha, Tokyo, Japan

[21] Appl. No.: 381,687

[22] Filed: Jan. 26, 1995

[30]  Foreign Application Priority Data

Jan. 26, 1994 [JP] Japan ................................ 6-006771
Feb. 21, 1994 [JP] Japan ................................ 6-022826
May 24, 1994 [JP] Japan ................................ 6-109985

[51] Int. Cl.$^6$ ................................ G01B 7/24; B05D 5/12
[52] U.S. Cl. ................................ 324/209; 427/8
[58] Field of Search ................................ 324/209, 228; 73/774, 775, 776, 763, 779; 340/551, 571, 572, 573; 427/8

[56]  References Cited

U.S. PATENT DOCUMENTS

| | | | |
|---|---|---|---|
| 3,636,437 | 1/1972 | Soulant, Jr. et al. | 324/209 |
| 3,792,348 | 2/1974 | Rollwitz et al. | 324/209 |
| 4,940,966 | 7/1990 | Pettigrew et al. | 340/551 |
| 5,047,717 | 9/1991 | Hofer | 324/209 |
| 5,175,419 | 12/1992 | Yamashita | 235/449 |
| 5,180,969 | 1/1993 | Kwun et al. | 324/71.2 |
| 5,268,043 | 12/1993 | McCowen | 148/310 |
| 5,297,439 | 3/1994 | Tyren et al. | 73/779 |
| 5,453,291 | 9/1995 | Sasahara et al. | 427/8 |

FOREIGN PATENT DOCUMENTS 9100494  1/1991  WIPO .

OTHER PUBLICATIONS

English language Abstract of JP 61201126 Jan. 28, 1987.
JP 3035136—English tranlsation of Abstract Jul. 3, 1989.
SU 1109579—English translation of Abstract Aug. 23, 1984.
JP 5142130—English translation of Abstract Jun. 8, 1993.
JP 2271227—English translation of Abstract Nov. 6, 1990.
JP 6155583—English translation of Abstract Jun. 3, 1994.
JP 6160355—English translation of Abstract Jun. 7, 1994.

*Primary Examiner*—Sandra L. O'Shea
*Assistant Examiner*—Roger Phillips
*Attorney, Agent, or Firm*—Lyon & Lyon LLP

[57]  ABSTRACT

In measuring a stress of a soft magnetic metal wire, an A.C. magnetic field exceeding a coercive force of the metal wire is applied to the soft magnetic metal wire with a tensile load applied thereto, using an exciting coil, thereby inducing an A.C. electromotive force through a detecting coil. An effective value of one or more higher harmonic wave components including a stress information of the soft magnetic metal wire in the waveform of the A.C. electromotive force is determined as a measurement amount. By taking higher harmonic wave components as an amount in this manner, the stress of the soft magnetic metal wire 4 can be measured correctly.

3 Claims, 14 Drawing Sheets

PROCESS FOR MEASURING STRESS OF MAGNETIC MATERIALS, FRP MEMBER WHOSE INTERNAL DAMAGE IS DETECTABLE, AND ADHESIVE LAYER FORMING ADHESIVE MEMBER WHOSE INTERNAL DEFECTION IS DETECTABLE

BACKGROUND OF THE INVENTION

1. Field of the Invention

The invention relates to a process for measuring the stress of a magnetic material, particularly, to an improvement in the process for measuring the stress of a magnetic material by utilizing a magneto-mechanical property of the magnetic material; an FRP (fiber-reinforced plastics) member whose internal damage is detectable, particularly, an FRP member whose internal damage can be detected by utilizing a magneto-mechanical property of a soft magnetic material; and an adhesive layer forming adhesive member whose internal defection is detectable, particularly, an adhesive member for forming an adhesive layer for bonding one member to another member, and for enabling detection of an internal defection thereof by utilizing a magneto-mechanical property of a soft magnetic material.

2. Description of the Prior Art

Such a stress-measuring process is conventionally known, which uses, as a measurement value, a variation in distribution of higher harmonic wave components including stress information concerning a magnetic material in an output signal, i.e., a ratio of outputs of two types of higher harmonic wave components (see Japanese Patent Application Laid-open No.201126/1986).

However, this prior art process has a problem in that the output ratio is varied such as to describe a curve having one peak with respect to a variation in stress. Therefore, notwithstanding that the stress of the magnetic material is different on opposite sides of a peak value, the same output ratio may be measured in some cases, resulting in inaccuracy.

An FRP member of the above-described type is known which includes a long carbon fiber embedded in an FOP member body (see Japanese Patent Application Laid-open No. 114741/1985).

Thus internal damage to this FRP member is detected by measuring an electric resistance of the long carbon fiber. This is based on a consideration that if an internal damage is produced in the FRP member, the long carbon fiber is broken, and the electric resistance value is varied.

However, this prior art FOP member has a problem in that it is impossible to detect a fine internal damage which is so small that it does not cause the breaking of the long carbon fiber, e.g., a hair crack produced in a plastics matrix surrounding the long carbon fiber, or an interfacial separation between the long carbon fiber and the plastics matrix.

Conventionally known methods for inspecting the adhesive layer include a performance test method according to the general rules of a weathering resistance test method defined in JIBS-K-6860, and a non-fracture inspecting method such as an ultrasonic damage searching method, and an X-ray method.

However, the performance test method is a method applied only to a test piece and hence it is very difficult to inspect an adhesive layer present between two bonded members. On the other hand, the non-fracture test method can provide an inspection result in its own way if it is applied to a test piece. However, the non-fracture test method is unsuitable for an adhesive layer of the above-described type, because there are many limitations to the shape, size and the like of the adhesive layer.

SUMMARY OF THE INVENTION

Accordingly, it is an object of the invention to provide a stress measure process of the above-described type, which can perform a correct measurement of the stress by detecting the stress of a magnetic material as an effective value of higher harmonic wave components including stress information, and thus as a measurement amount.

To achieve the above object, according to the invention, there is provided a process for measuring a stress of a magnetic material, comprising the steps of: applying, to a magnetic material as a subject to be measured, an A.C. magnetic field exceeding a coercive force of the magnetic material by use of an exciting coil so as to induce an A.C. electromotive force in a detecting coil through the magnetic material; and determining, as a measurement amount, an effective value of one or more higher harmonic wave components including stress information of the magnetic material in the waveform of the A.C. electromotive force.

In addition, according to the invention, there is provided a process for measuring stress of a magnetic material, comprising the steps of: applying, to a magnetic material as a subject to be measured, an A.C. magnetic field exceeding a coercive force of the magnetic material by use of an exciting coil so as to induce an A.C. electromotive force in a detecting coil through the magnetic material; and determining, as a measurement amount, a distortion factor of one or more higher harmonic wave component including stress information concerning the magnetic material in the waveform of the A.C. electromotive force.

As described above, if the effective value or the distortion factor of the one or more higher harmonic wave components including stress information of the magnetic material is determined as a measurement amount, i.e., if the higher harmonic wave components are taken as an amount, the stress of the magnetic material can be measured with a high accuracy and therefore, a very small variation in stress can be detected.

It is another object of the invention to provide an FRP member of the above-described type, which is formed so that a very small internal damage of the above-described type can also be detected correctly.

To achieve the above object, according to the invention, there is provided an FRP member whose internal damage is detectable by utilizing a magneto-mechanical property of a soft magnetic material, the FRP member comprising an FRP member body and a plurality of the soft magnetic materials, the soft magnetic materials being embedded in the FRP member body so as to form a single layer extending along a surface of the FRP member body, and held in a state subjected to an external force.

If the plurality of soft magnetic materials is mounted to form a layer extending along one surface of the FRP member body, the stress of the soft magnetic materials can be measured from the surface side of the member body with good accuracy.

If a hair crack is produced in a plastics matrix within the FRP member body, or an interfacial separation is produced between the plastics matrix and the soft magnetic materials, the binding force acting on the soft magnetic materials and thus the originally applied external force is decreased and the stress of the soft magnetic materials is correspondingly decreased, whereby even a very small internal damage of the FRP member can be detected.

In this case, the soft magnetic materials are disposed at equal short distances from the surface of the FRP member body and therefore, the level of a signal outputted from the soft magnetic materials that pertains to an internal information of the FRP member is high, whereby the presence or absence of an internal damage can be detected with a high sensitivity.

For example, if the plurality of soft magnetic materials is disposed within the FRP member body so as to form two or more layers extending along one surface of the FRP member body, a damage is liable to be produced in the vicinity of the surface of the FRP member due to the magnitude of a strain provided when a flexure is produced in the member. When a damage has been produced in the vicinity of the surface of the FRP member, if there is another soft magnetic material located at a non-damaged area deeper than the location where such damage occurs, a wholesome information is also simultaneously detected and for this reason, an internal damage information becomes vague.

The application of the external force to the soft magnetic materials is easily realized using a difference in thermal expansion coefficient between the FRP member body and the soft magnetic materials upon curing of the plastics matrix by heating, but as an alternative, a method comprising embedding the soft magnetic materials in the plastics matrix in their tension-applied states may be employed.

Further, it is an object of the invention to provide an adhesive member of the above-described type, which is capable of forming, between various members to be bonded, an adhesive layer whose internal defection can be detected in a non-invasive state.

To achieve the above object, according to the invention, there is provided an adhesive member for forming an adhesive layer for bonding one member and another member to each other to provide an integrated article, and for detecting an internal defection in the adhesive layer by utilizing a magneto-mechanical property of a soft magnetic material, the adhesive member comprising a main body formed of an uncured adhesive and a plurality of the soft magnetic materials embedded in the main body, the soft magnetic materials being held in a state subjected to an external force after curing of the main body.

When the one member is bonded to the other member using the above-described adhesive member, the stress of the soft magnetic materials can be measured with good accuracy from a surface of any one member to be bonded by utilizing the magneto-mechanical property of the soft magnetic materials, because the plurality of soft magnetic materials is embedded within the adhesive layer with a predetermined stress given thereto.

On the other hand, if an internal defection such as a crack is produced in the main body of the cured adhesive layer, the binding force acting on the soft magnetic materials and thus the originally applied external force is decreased and hence the stress of the soft materials are also correspondingly decreased, whereby any internal defection of the adhesive layer can be easily detected in a non-broken state.

Immediately after bonding of both the members, the stress of the soft magnetic materials is detected along the surface of either one of the members, and if there is a portion having an abnormal detected stress value, such portion is regarded as a defectively or insufficiently bonded portion. In this manner, the adhesive member may also be used for judging whether or not the adhesive layer formed therefrom is wholesome.

For example, if the main body is formed of an uncured thermosetting synthetic resin-based adhesive and has an extremely thin thickness, and the bonded members have a thermal expansion coefficient different from that of the soft magnetic materials, the application of the external force to the soft magnetic materials is realized because of a difference in thermal expansion coefficient between the soft magnetic materials and the bonded members. But a method for curing the main body in a condition in which a tension has been applied to the soft magnetic materials may be employed.

The above and other objects, features and advantages of the invention will become apparent from the following description of preferred embodiments taken in conjunction with the accompanying drawings.

DESCRIPTION OF THE PREFERRED EMBODIMENTS

First, the principle of a stress measuring process according to the invention will be described.

Figure 1:
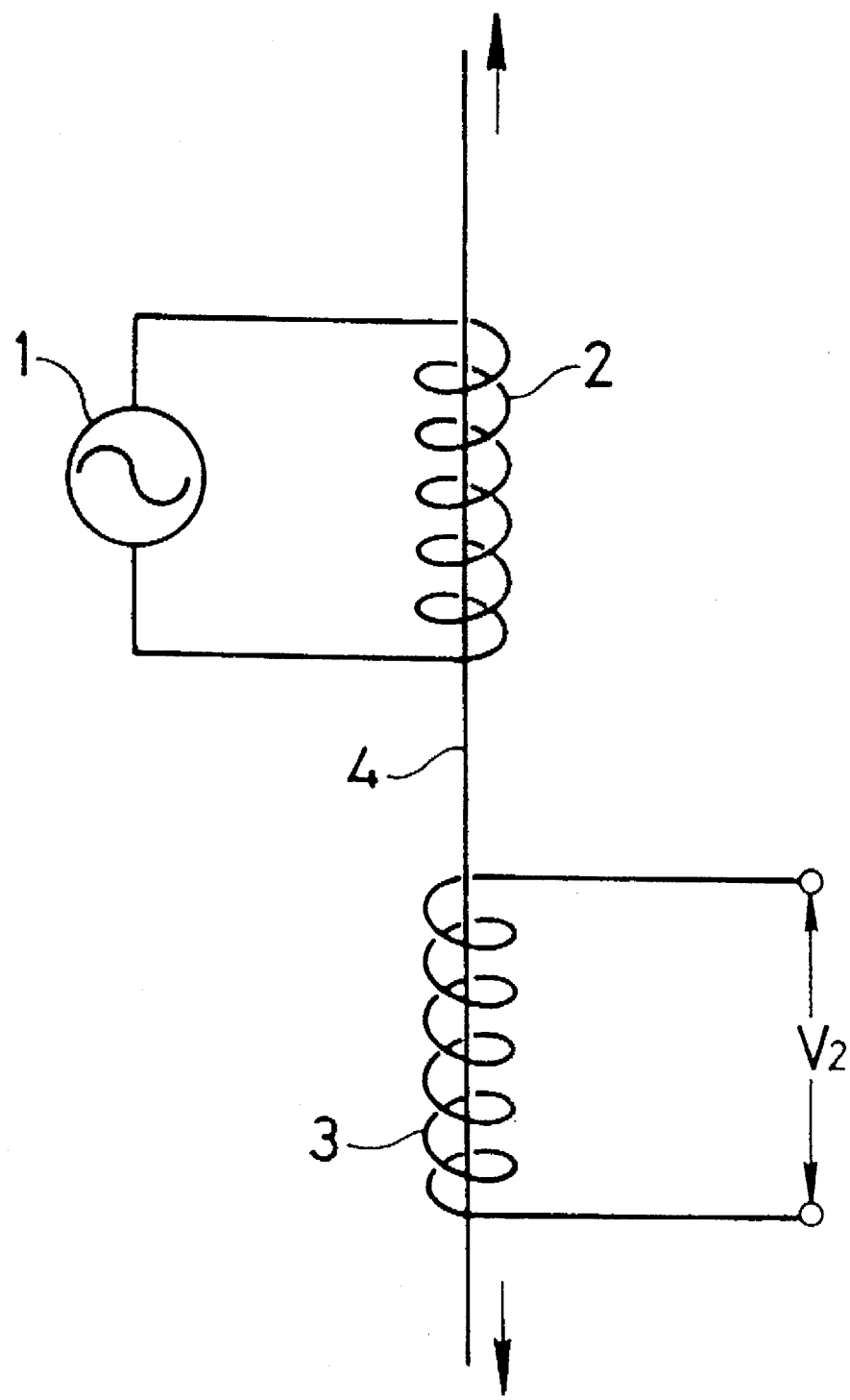
FIG. 1 is an illustration of the principle of a stress measuring process.

Referring to FIG. 1, a soft magnetic metal wire 4 as a magnetic material is inserted through an exciting coil 2 connected to an oscillator 1 and through a detecting coil 3. A predetermined tension load is applied to the metal wire 4.

If the oscillator 1 is operated to apply, to the metal wire 4, an A.C. magnetic field H exceeding a coercive force Hc of the metal wire 4 and including no D.C. magnetic field component by the exciting coil 2, an A.C. electromotive force $V_2$ which is symmetric in plus and minus is induced in the detecting coil 3 through the metal wire 4.

Here, the A.C. electromotive force $V_2$ is represented by the following expression:

$$V_2 = -\frac{d\phi}{dt} = -\alpha \left(1 + 4\pi \frac{dI}{dH}\right) \frac{dH}{dt} \qquad (1)$$

wherein $\phi$ is a magnetic flux; t is time; $\alpha$ is a coefficient; I is an intensity of magnetization of the metal wire 4; and H is an intensity of the A.C. magnetic field.

The A.C. magnetic field H is represented by the following expression (2):

$$H = Hm \cdot \sin(2\pi f_0 t + \phi 0) \qquad (2)$$

wherein Am is an amplitude of the A.C. magnetic field H; $f_0$ is a frequency; and $\phi_0$ is a phase angle.

Here, the expression (2) is differentiated by the time t to provide an expression (3):

$$\frac{dH}{dt} = 2\pi f_0 Hm \cdot \cos(2\pi f_0 t + \Phi o). \qquad (3)$$

If HD/dt in the expression (3) is substituted into the expression (1), the A.C. electromotive force $V_2$ is represented by the following expression (4):

$$V_2 = -2\pi\alpha f_0 Hm \left(1 + 4\pi \frac{dI}{dH}\right) \cos(2\pi f_0 t + \Phi o) \qquad (4)$$

Figure 2:
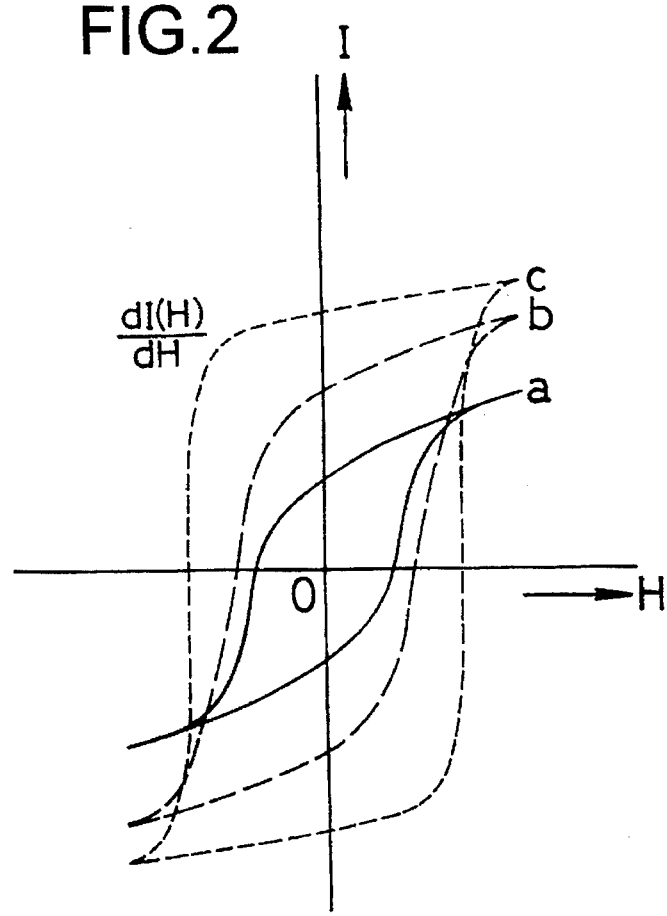
FIG. 2 is a diagram of magnetization curves for soft magnetic metal wires.

In the course of magnetization of the sot magnetic metal wire 4, a magnetization curve as shown by a line a in FIG. 2 is obtained and hence the expression (4) is represented by a following expression (5) using an instantaneous magnetization rate dI(H)dh:

$$V_2 = -2\pi\alpha f_0 Hm \left(1 + 4\pi \frac{dI(H)}{dH}\right) \cos(2\pi f_0 t + \Phi o) \qquad (5)$$

Figure 3:
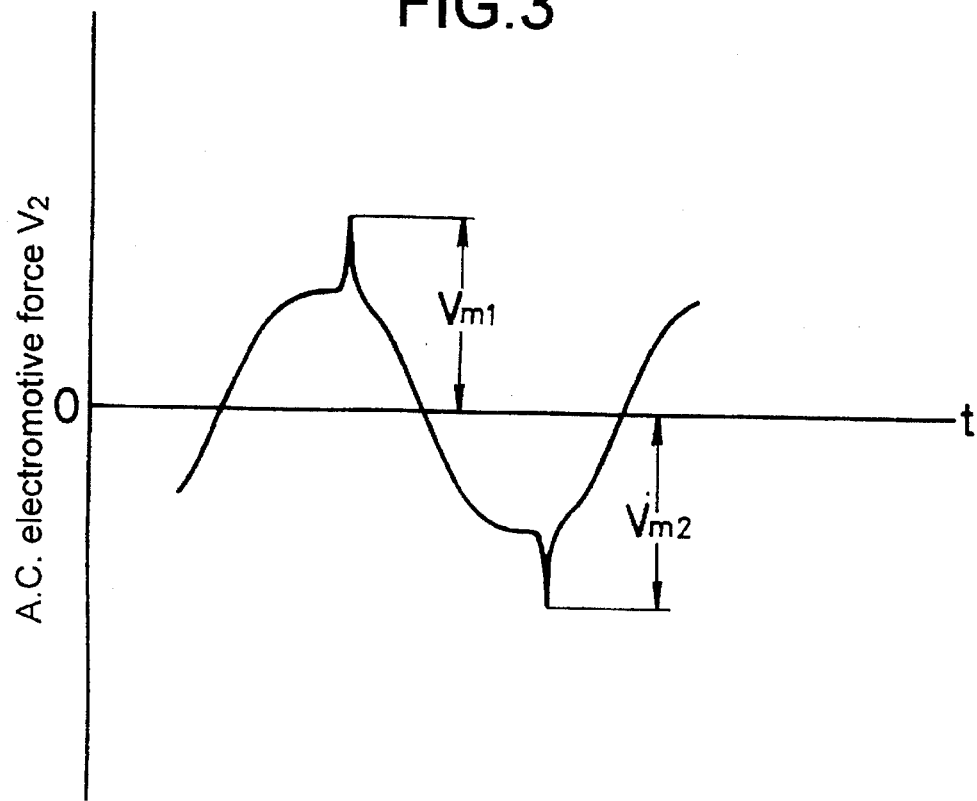
FIG. 3 is a waveform diagram of an A.C. electromotive force $V_2$.

The A.C. electromotive force $V_2$ includes a higher harmonic wave component, because the waveform thereof is of a distorted wave, as shown in FIG. 3. In this case, the A.C. magnetic field H includes no D.C. magnetic field component, as described above and therefore, the higher harmonic wave component of the A.C. electromotive force $V_2$, in principle, consists of only an odd harmonic wave component and includes no even harmonic wave component.

The higher harmonic wave component is dependent upon the instantaneous magnetization rate dI(H)/dH which is dependent upon a stress of the metal wire 4. Therefore, the higher harmonic wave component includes a stress information of the metal wire 4.

Thereupon, the waveform of the A.C. electromotive force $V_2$ is subjected to a frequency analysis using a spectral analyzer for division into fundamental wave component and a higher harmonic wave component to determine effective values Ev1 and Ev2 or a distortion factor K of one or more higher harmonic wave components as a measurement amount of the stress of the metal wire 4.

For example, when the higher harmonic wave components are third, fifth, seventh and ninth harmonic wave components, the effective value Ev1 thereof is represented by the following expression (6):

$$Ev1 = \sqrt{E_3^2 + E_5^2 + E_7^2 + E_9^2} \qquad (6)$$

wherein $E_3$, $E_5$, $E_7$ and $E_9$ are effective values of the third, fifth, seventh and ninth harmonic wave components, respectively. The calculation of the effective value Ev1 is carried out using a calculator.

When a certain harmonic wave component sufficiently and correctly includes a stress information of the metal wire, its effective value Ev2 may simply be used as a stress measurement amount. In this case, such effective value Ev2 can be outputted by connecting a narrow-band filter corresponding to such harmonic wave component to the detecting coil 3.

The distortion factor K is represented by the following expression (7):

$$K = \frac{\sqrt{E_3^2 + E_5^2 + E_7^2 + E_9^2}}{E_1} \qquad (7)$$

wherein $E_1$ is an effective value of the fundamental wave component. The calculation of this distortion factor K is carried out using a calculator.

On the other hand, the magnetic characteristic of the metal wire 4 is varied in response to the change in a condition in which the metal wire 4 is placed. Namely, if the tension load on the metal wire 4 is varied from a large value to a small value, the instantaneous magnetization rate dI(H)dH of the metal wire 4 is varied from a large value to a small value, as line c→line b →line a in FIG. 2. As a result, $V_2(t)$ which is a periodic function is varied and hence the effective value of the higher harmonic wave components is also varied.

Figure 4:
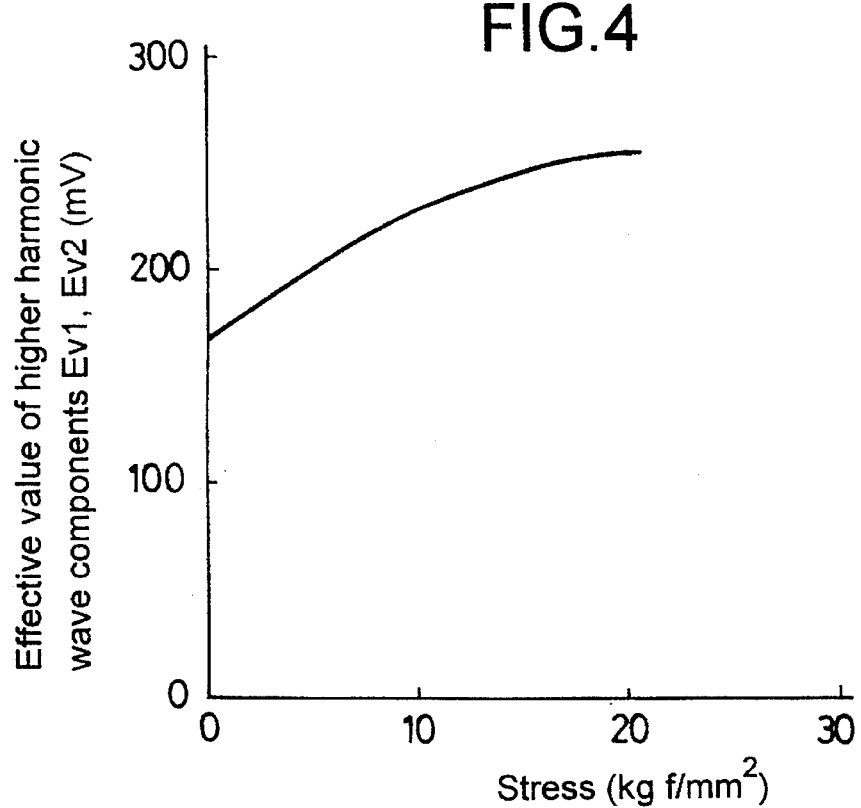
FIG. 4 is a graph illustrating the relationship between the stress and the effective values Ev1 and Ev2 of higher harmonic wave components.
Figure 5:
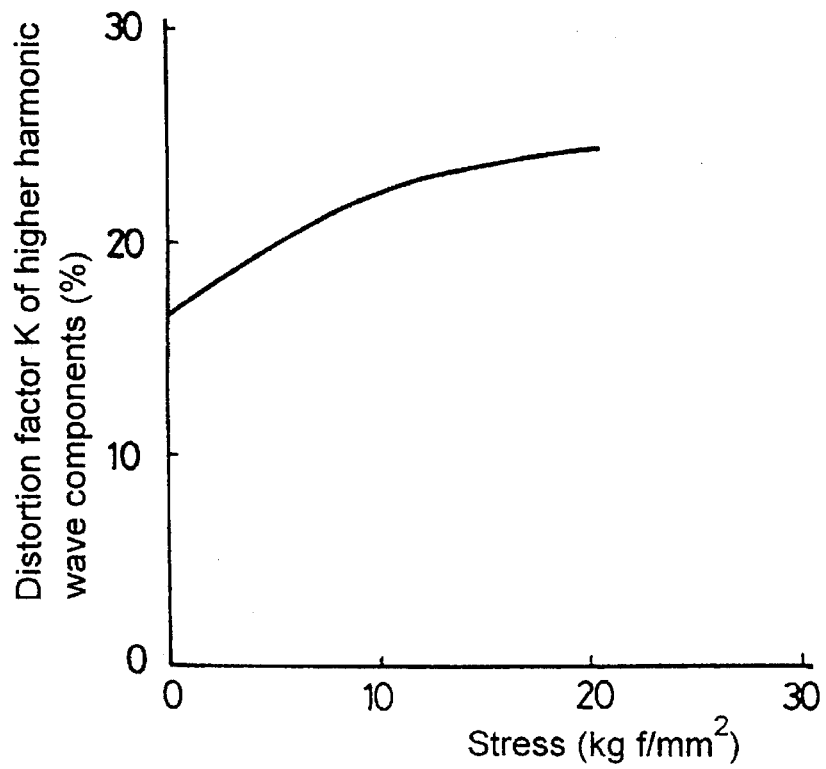
FIG. 5 is a graph illustrating the relationship between the stress and the the distortion factor K of the higher harmonic wave components.

Therefore, a minute variation in stress of the metal wire 4 can be correctly measured, as shown in FIGS. 4 and 5.

EXAMPLE 1

Figure 6:
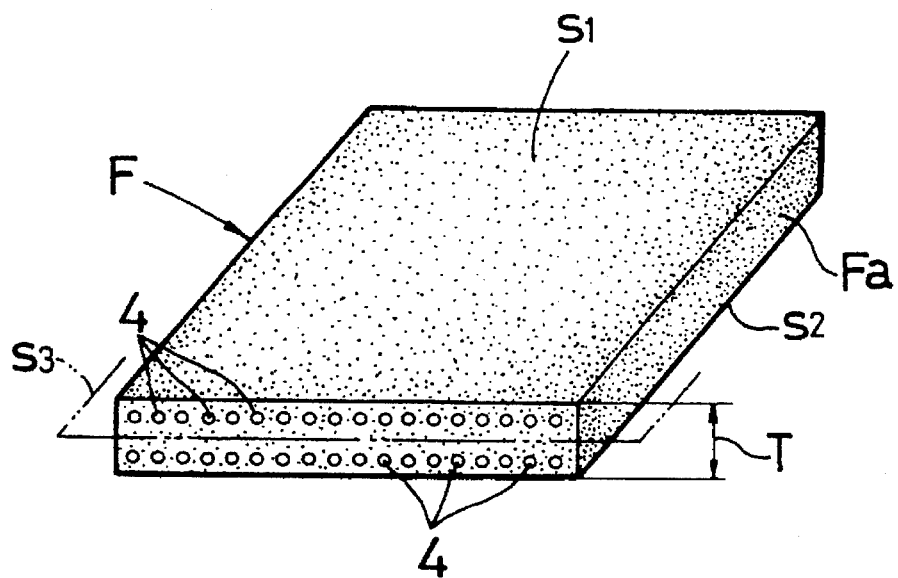
FIG. 6 is a perspective view of one example of an FRP member having amorphous metal wires embedded therein.

An FRP member F shown in FIG. 6 is used for judging the presence or absence and degree of an internal damage due to a fatigue. The FRP member F capable of detecting the internal damage is of a plate-like shape and composed of an FRP member body Fa, a plurality of soft magnetic metal wires 4 as soft magnetic materials embedded in the FRP member body Fa so as to form a single layer extending along one surface $s_1$ of the FRP member body Fa, and a plurality of soft magnetic metal wires 4 as soft magnetic materials embedded in the FRP member body Fa so as to form a single layer extending along another surface $s_2$ of the FRP member body Fa. Each of the metal wires 4 is bound to a state in which an external force, e.g., a tension load (in this example) has been applied thereto.

The FRP member body Fa is formed from a carbon fiber as a reinforcing fiber and an epoxy resin as a plastic matrix.

The soft magnetic metal wire is formed of an amorphous metal wire 4. The amorphous metal wires 4 on each side of the surfaces $S_1$ and $S_2$ are arranged parallel to each other at given distances therebetween in the FRP member body Fa.

The plurality of amorphous metal wires 4 arranged parallel at the given distances to form the single layer extending along the one surface $s_1$ and the plurality of amorphous metal wires 4 arranged parallel at the given distances to form the single layer extending along the other surface $s_2$ are arranged in a plane-symmetric relation to each other with respect to a phantom division plane $s_3$ which equally divides the thickness T of the FRP member body Fa into two portions.

If the amorphous metal wires 4 are arranged into a layered configuration at the sides of the surfaces $s_1$ and $s_2$ of the FRP member body Fa, the FRP member F has the same sectional structure at the sides of the surface $s_1$ and $s_2$ and therefore, a warping of the FRP member F can be prevented.

Figure 7:
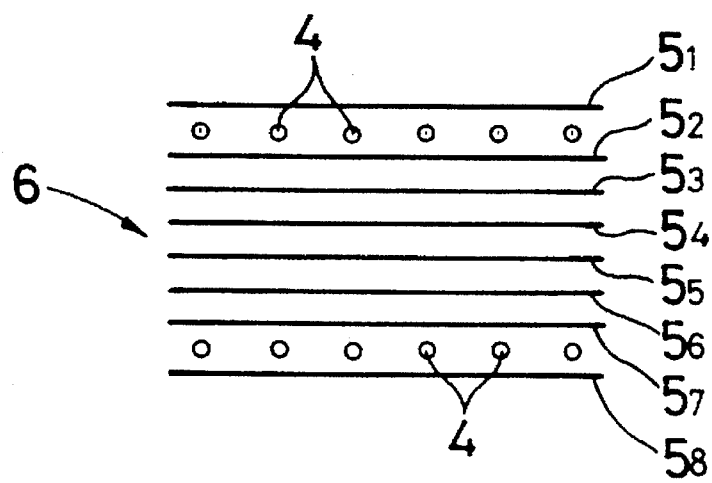
FIG. 7 is a diagram illustrating one example of the relationship between carbon fiber cloths and the amorphous metal wires in the FRP member.

The FRP member F was fabricated in the following manner. As shown in FIG. 7, eight cloths $5_1$ to $5_8$ made of carbon fiber having a diameter of 6 μ were laminated, such that the orientations of the carbon fibers in the adjacent cloths $5_1$ and $5_2$ or the like were offset by 45° from each other. A plurality of amorphous metal wires 4 having a diameter of 120 μm were arranged parallel at a pitch of 0.3 mm between the first and second cloths $5_1$ and $5_2$ and between the seventh and eighth cloths $5_7$ and $5_8$. The amorphous metal wire 4 has a composition of $Fe_{66.5}Si_{8.5}B_{12}Co_{11}Cr_2$ (wherein each of the numerical values is by atom %) and a coercive force Hc of 0.6 oersted.

A laminated body 6 of the cloths $5_1$ to $5_8$ and the amorphous metal wires 4 was impregnated with an epoxy resin solution and subjected to a heating treatment at 180° C. for 2 hours to cure the epoxy resin, thereby producing an FRP member F including an FRP member body Fa having an epoxy resin matrix and the carbon fiber, and the plurality of amorphous metal wires 4 embedded in the FRP member body Fa to form a single layer in each of the surfaces $s_1$ and $s_2$, as shown in FIG. 6.

In this case, the amorphous metal wire 4 has a thermal expansion coefficient of about $7 \times 10^{-6}/°C$., and the FRP member body Fa has a thermal expansion coefficient of about $4 \times 10^{-6}/°C$. Therefore, after the curing of the epoxy resin by heating, each of the amorphous metal wires 4 is bound to a state in which a tension load has been applied thereto. If the amorphous metal wire 4 is magnetized, a so-called magnetostriction phenomenon producing an elongation in the metal wire 4 is generated. However, the magnetostriction oscillation phenomenon under an A.C. magnetic field is suppressed by the carbon fiber and the cured epoxy resin.

In this FRP member F, the volume fraction Vf of the carbon fiber was 58.3%; the volume fraction Vf of the epoxy resin was 37.5%, and the volume fraction Vf of the amorphous metal wires 4 was 4.2%.

Figure 8:
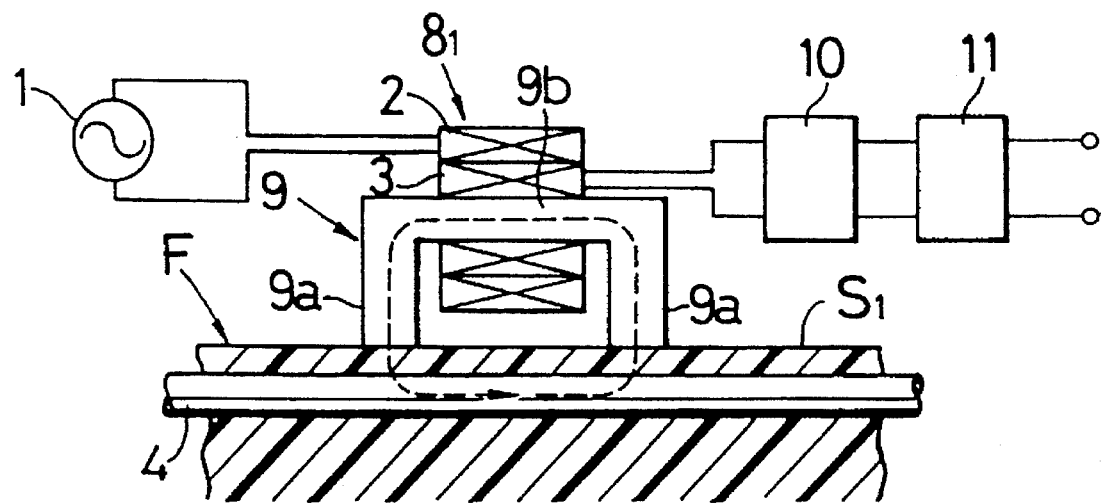
FIG. 8 is a schematic view illustrating a first example of a stress measuring device and a stress measuring process.

FIG. 8 illustrates one example of a stress measuring device $8_1$. This device $8_1$ is constructed in the following manner. A ferrite core 9 is formed into a U-shape from a pair of legs $9a$ and a connecting portion $9b$ which connects one ends of both the legs $9a$ to each other. The detecting coil 3 is wound 100 turns (10 turns/mm) around the connecting portion $9b$, and the exciting coil 2 is wound 100 turns (10 turns/mm) around an outer periphery of the detecting coil 3. The exciting coil 2 is connected to the oscillator 1. The detecting coil 3 is connected to a spectral analyzer 10 which is connected to a calculator 11.

Figure 9:
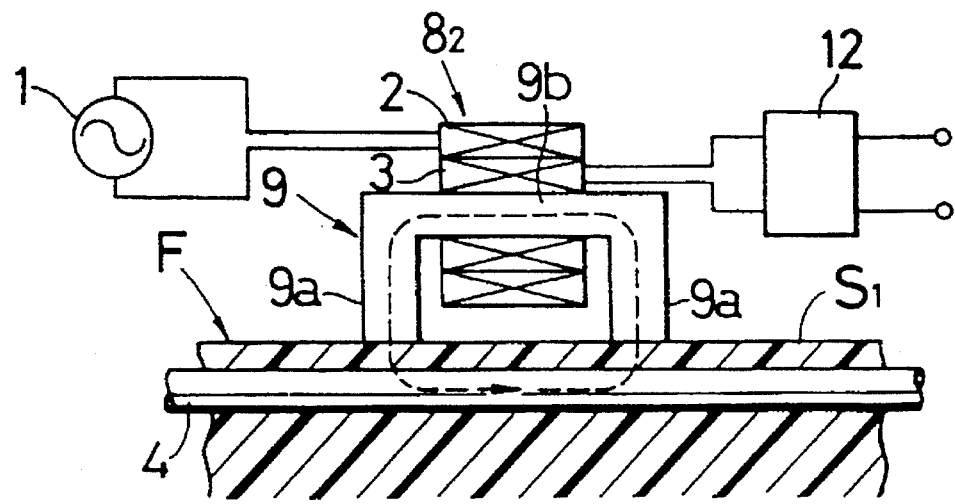
FIG. 9 is a schematic view illustrating a second example of a stress measuring device and a stress measuring process.

FIG. 9 illustrate another example of the stress measuring device $8_2$. The stress measuring device $8_2$ has the narrowband filter 12 connected to the detecting coil 3, in place of the spectral analyzer 10 and the calculator 11 in the device $8_1$ shown in FIG. 8. Other arrangement is the same as in the device $8_1$, shown in FIG. 8.

Figure 10:
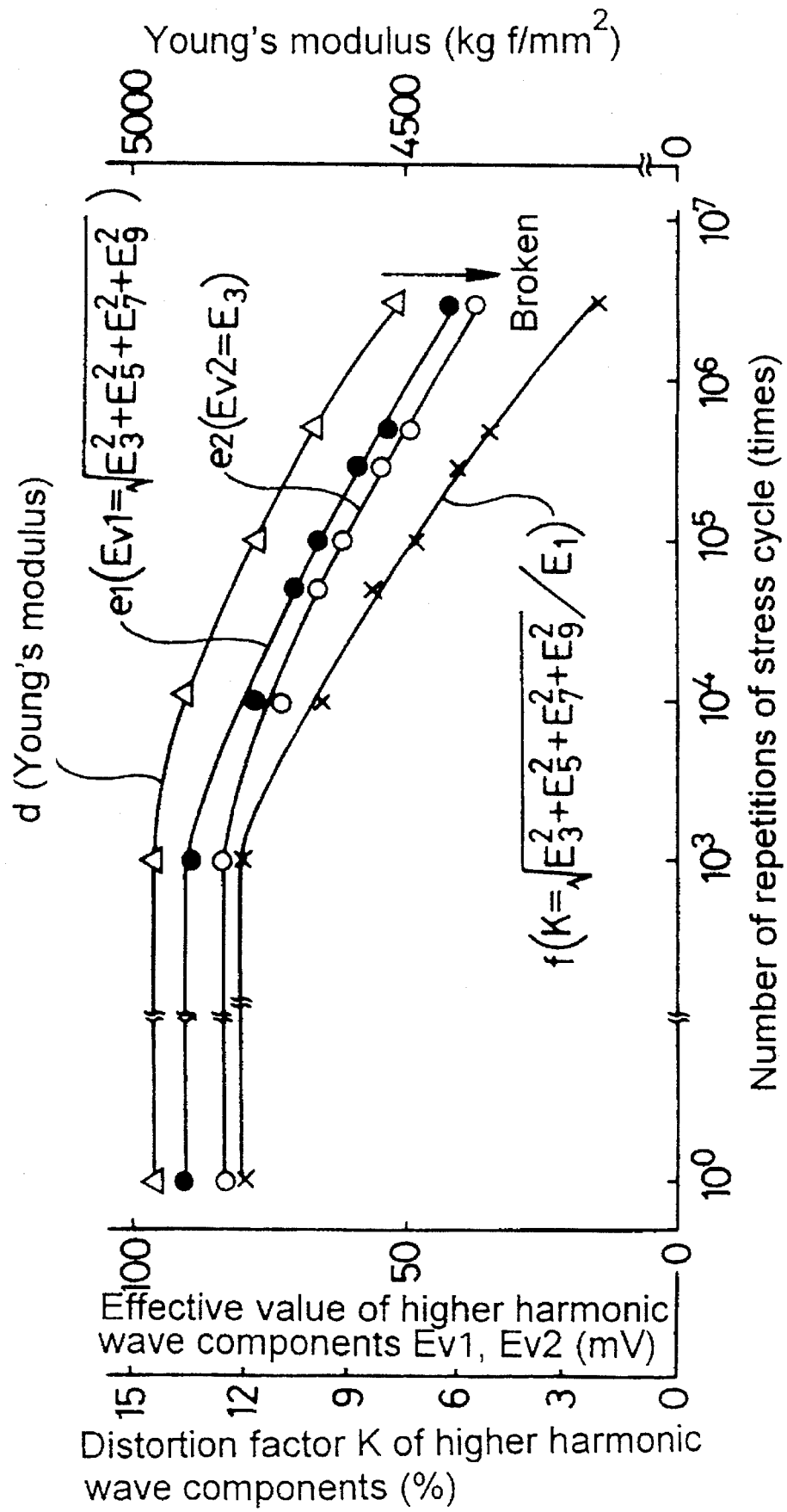
FIG. 10 is a graph illustrating the relationship between the number of repetitions of a stress cycle and the Young's modulus as well as the effective values Ev1 and Ev2 and the distortion factor K of higher harmonic wave components.

First, the FRP member F was subjected to a tension-tensile fatigue test to determine a relationship between the number of repetitions of a stress cycle and the Young's modulus, thereby providing a result shown by a line d in FIG. 10.

Conditions for this fatigue test are of a minimum tension load of 3 kgf/mm$^2$, a maximum tension load of 25 kgf/mm$^2$, and a repetition frequency of 20 Hz.

For the line d in FIG. 10, the FRP member F is not damaged and hence the Young's modulus thereof is not varied until the number of repetitions of the stress cycle reaches $10^3$. But when the number of repetitions of the stress cycle exceeds $10^3$, cracks are produced in the interior of the FRP member F, and an interfacial separation between the carbon fiber as well as the amorphous metal wires 4 and the epoxy resin matrix are produced, and hence, the Young's modulus starts lowering. The lowering phenomenun of the Young's modulus is promoted substantially proportionally with an increase in number of repetitions of the stress cycle, and at the number of repetitions of the stress cycle equal to $5 \times 10^6$, the FRP member F is broken.

Next, the FRP member F was subjected to a similar fatigue test to measure a stress of the amorphous metal wire 4 at every predetermined number of repetitions of the stress cycle.

In measuring the stress of the amorphous metal wire 4, end faces of both the legs $9a$ of the core 9 were placed against the one surface $s_1$ of the FRP member F, and the oscillator 1 was operated under oscillation conditions where a frequency of a sine wave including no D.C. magnetic field component is 1 kHz and a voltage between peaks, namely, a voltage between peaks in one period, is 15 $V_{p-p}$, thereby applying an A.C. magnetic field H exceeding a coercive force Hc of the amorphous metal wire 4 to the exciting coil 2. This caused a magnetic path to be formed between the core 9 and the amorphous metal wires 4, whereby an A.C. electromotive force $V_2$ was induced in the detecting coil 3. This A.C. electromotive force $V_2$ was applied to the spectral analyzer 10 and then, an effective value Ev1 of third, fifth, seventh and ninth harmonic wave components which were higher harmonic wave components, i.e., a value determined according to the above described expression (6), i.e., Ev1= $\sqrt{E_3^2+E_5^2+E_7^2+E_9^2}$, was outputted and determined as a measurement amount of the stress of the amorphous metal wires 4.

A relationship between the number of repetitions of the stress cycle and the effective value Ev1 was found as shown by a line $e_1$ in FIG. 10.

In the line $e_1$ in FIG. 10, the effective value Ev1 is constant until the number of repetitions of the stress cycle reaches $10^3$. It can be seen from this that the FRP member F was not damaged. If the number of repetitions of the stress cycle exceeds $10^3$, the effective value Ev1 starts lowering.

This is because cracks are produced within the FRP member F and hence, the binding force on the amorphous metal wire 4 is reduced and due to this, the stress of the amorphous metal wires is reduced, and the suppression of the magnetostriction oscillation phenomenon under the A.C. magnetic field is moderated. It can be seen from this that an internal damage was produced in the FRP member F.

When the number of repetitions of the stress cycle is further increased beyond $10^3$, the effective value Ev1 is lowered with a gradient substantially equivalent to that of a reduction in Young's modulus of the FRP member F. In other words, the effective value Ev1 precisely indicates the degree of the internal damage of the FRP member F.

Therefore, it is possible to correctly know the presence or absence and degree of the internal damage of the FRP member F by measuring the stress of the amorphous metal wires 4 embedded in the FRP member F.

A line $e_2$ in FIG. 10 illustrates a result obtained through the measuring of the stress using the stress measuring device $8_2$ shown in FIG. 9, wherein an effective value of a third harmonic wave component Ev2=$E_3$ was used as a measurement amount of the stress of the amorphous metal wires 4, because the third harmonic wave component sufficiently and correctly includes the stress information for the amorphous metal wires. Even in this case, it can be seen that this result is similar to that provided when the effective value Ev1 is used as the measurement amount of the stress.

A line f in FIG. 10 illustrates a result obtained through the measuring of the stress using the stress measuring device $8_1$ shown in FIG. 8, wherein a distortion factor K of higher harmonic wave components and thus third, fifth, seventh and ninth harmonic wave components, i.e., a value determined according to the following expression (7), i.e., $$K = \frac{\sqrt{E_3^2 + E_5^2 + E_7^2 + E_9^2}}{E_1},$$

was used as a measurement amount of the stress of the amorphous metal wires 4. Even in this case, a tendency is observed which is similar to that when the effective values Ev1 and Ev2 were used as measurement amounts of the stress.

Figure 11:
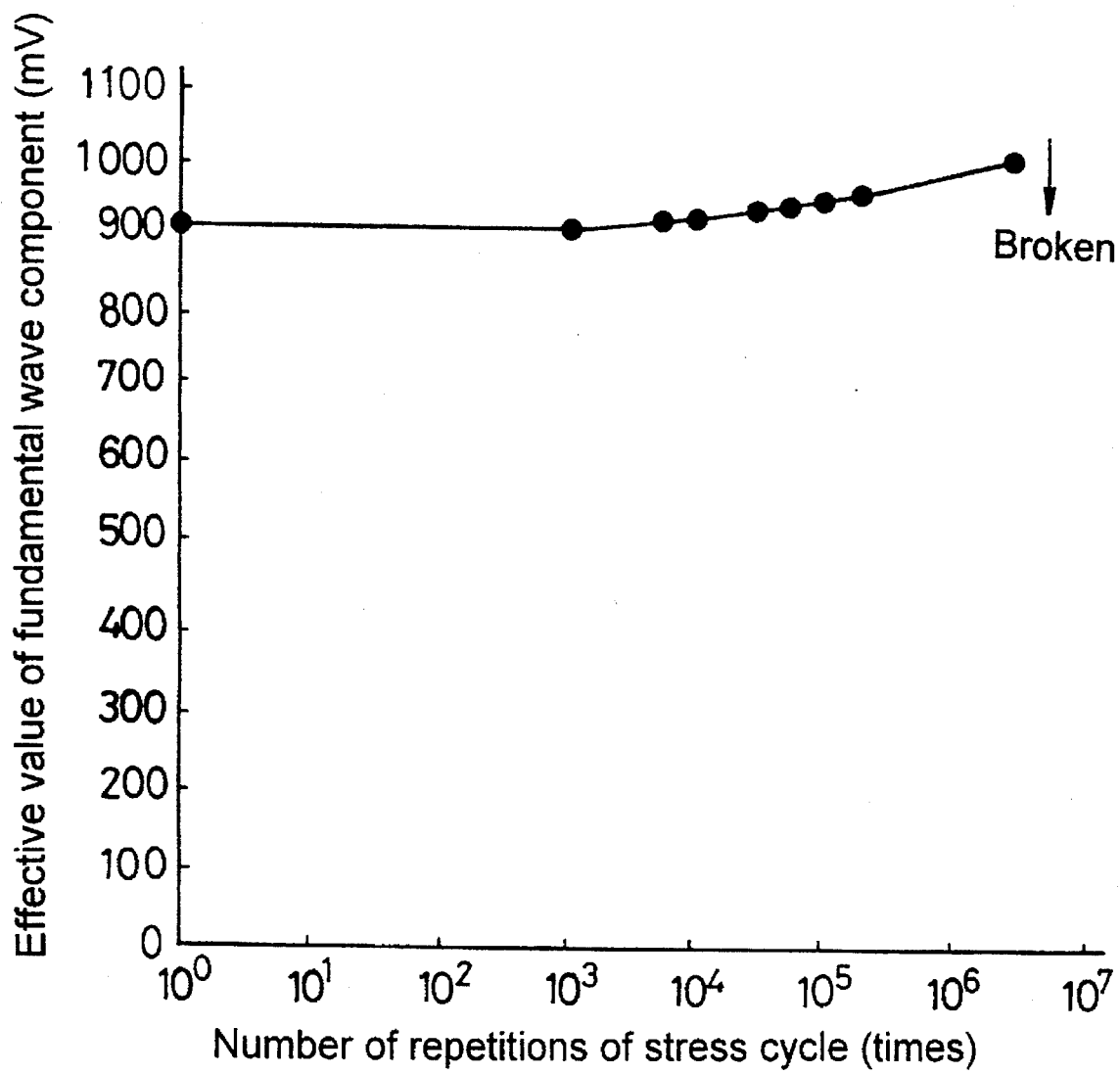
FIG. 11 is a graph illustrating the relationship between the number of repetitions of the stress cycle and the effective value $E_1$ of a fundamental wave component.

For the FRP member F including the amorphous metal wires 4, if the number of repetitions of the stress cycle exceeds $10^3$, the effective value Ev1 in the numerator in the expression (7), namely, higher harmonic wave components, is decreased, and the effective value $E_1$ in the denominator in the expression (7), namely, fundamental wave components, is increased, as shown in FIG. 11.

For this reason, a reduction rate of the distortion factor K when the number of repetitions of the stress cycle exceeds $10^3$ is larger than that of the effective value. Therefore, in measuring the internal damage of the FRP member F of the above-described construction, a measurement of a higher sensitivity can be performed by using the distortion factor K as a measurement amount.

Figure 12:
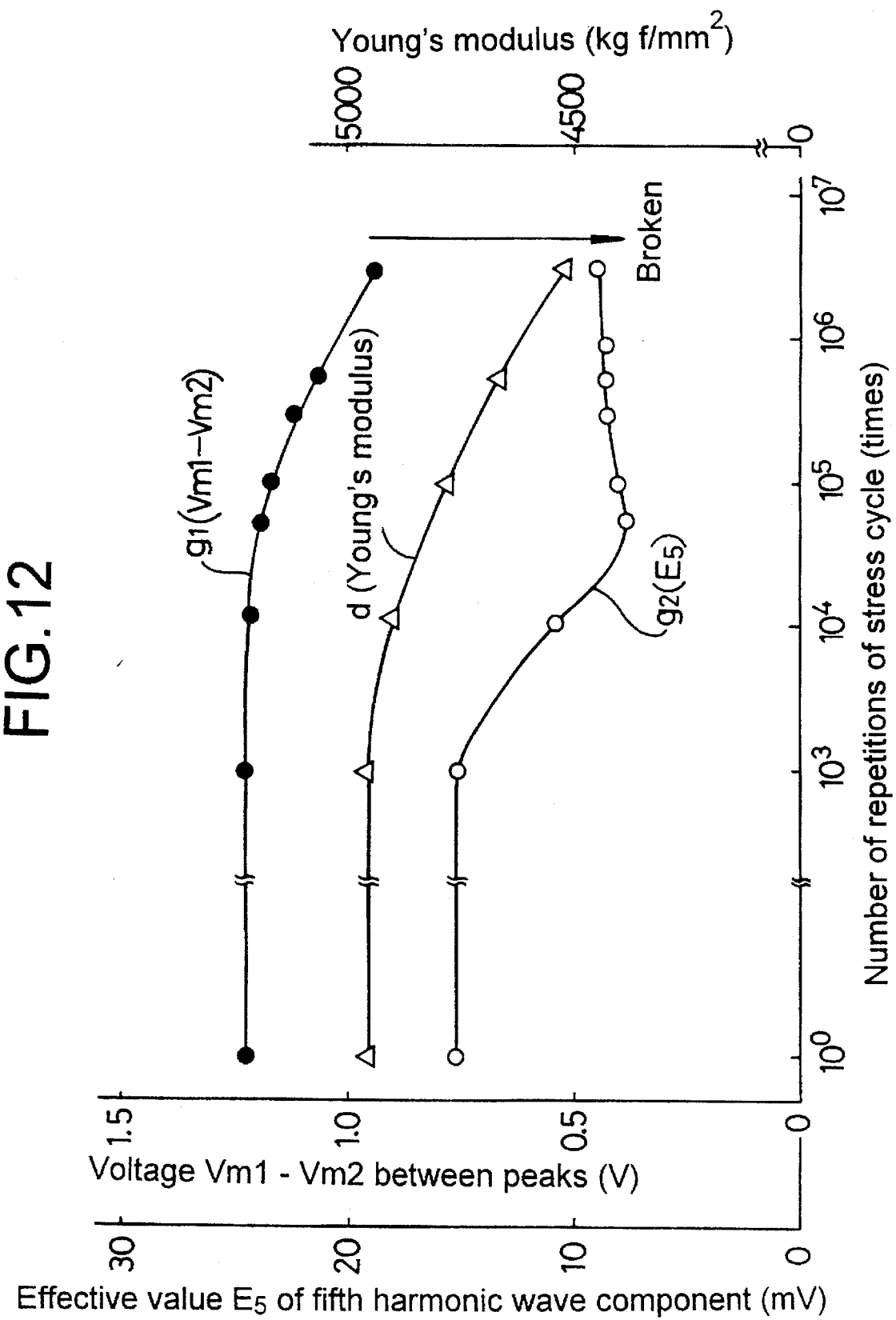
FIG. 12 is a graph illustrating the relationship between the number of repetitions of the stress cycle and the Young's modulus, the voltage between peaks Vm1–Vm2 as well as the effective value $E_5$ of a fifth harmonic wave component.

FIG. 12 illustrates a comparative example, wherein a line $g_1$ shows a result obtained when a voltage between peaks Vm1–Vm2 shown in FIG. 3 was used as a measurement amount of the stress of amorphous metal wires 4, and a line $g_2$ shows a result obtained when an effective value Ev5 of the fifth harmonic wave component was used as a measurement amount of the stress of amorphous metal wires 4.

With respect to the line $g_1$, a variation around a turning point at about 10 times repetition of the stress cycle is unclear. With respect to the line $g_2$, a turning point around about $10^3$ times repetition is clear, but this line shows an irregular variation that the effective value $E_5$ once decreased starts increasing from the number of repetitions of stress cycle of about $7.5 \times 10^4$. Therefore, notwithstanding that the stresses of the amorphous metal wires 4 are difficult to measure on opposite sides of the minimum effective value, the same effective value may be obtained in some cases. This makes it impossible to correctly find the degree of the internal damage of the FRP member F, if the stress cycle is repeated, for example, more than about $3 \times 10^4$.

Figure 13:
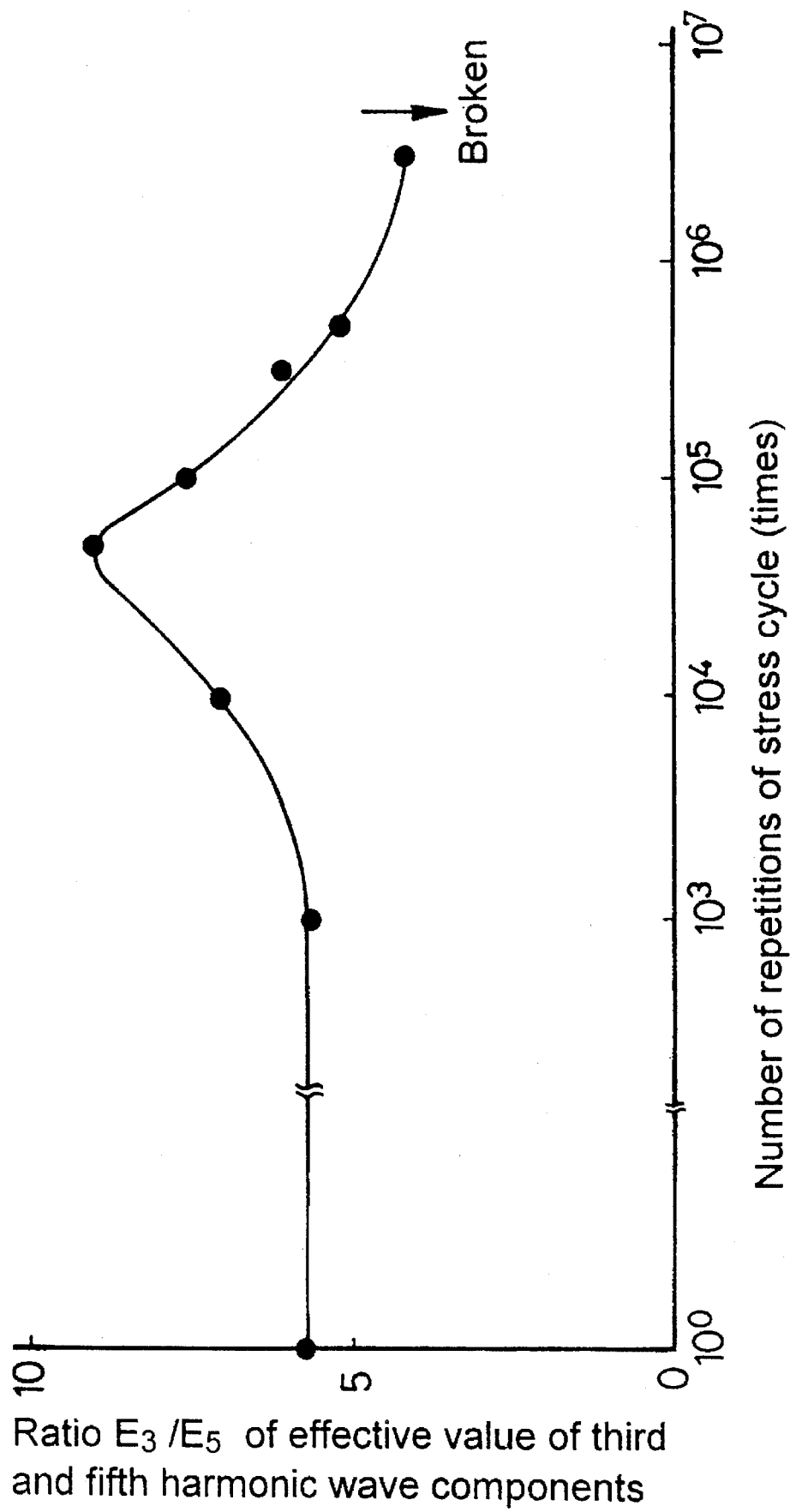
FIG. 13 is a graph illustrating the relationship between the number of repetitions of the stress cycle and the ratio $E_3/E_5$ of effective values of third and fifth harmonic wave components.

FIG. 13 illustrates another comparative example corresponding to the prior art example, wherein a ratio $E_3/E_5$ between the effective values $E_3$ and $E_5$ of the third and fifth harmonic wave components was used as a measurement value of the stress of the amorphous metal wires 4. Even in this case, notwithstanding that the stresses of the amorphous metal wires 4 are difficult to measure on opposite sides of a peak value, the same ratio $E_3/E_5$ was obtained and hence a disadvantage similar to that described above occurred.

Figure 14:
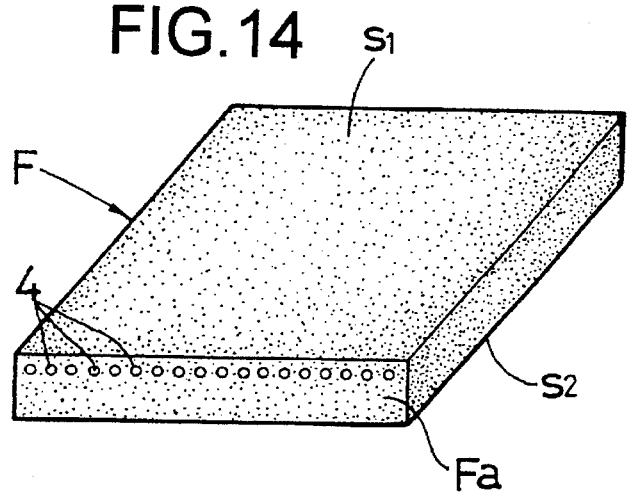
FIG. 14 is a perspective view illustrating another example of an FRP member having amorphous metal wires embedded therein.

FIG. 14 illustrates another example of an FRP member F whose internal damage can be detected. This FRP member F is of a plate-like shape and includes an FRP member body Fa, and a plurality of amorphous metal wires 4 embedded in the FRP member body Fa to form a single layer extending along one surface $s_1$ of the FRP member body Fa. Each of the amorphous metal wires 4 is bound to a state in which an external force, e.g., a tension load in this example as in the above-described example, has been applied thereto. The amorphous metal wires 4 are arranged parallel to each other at given distances therebetween.

In FIGS. 6 and 14, the amorphous metal wires 4 may be embedded in the FRP member body Fa, such that a portion of an outer peripheral surface of each amorphous metal wire 4 is exposed from the surfaces $s_1$ and $s_2$ of the FRP member body Fa.

EXAMPLE 2

An FRP member F was fabricated in the same manner as the FRP member F shown in FIG. 6, except that amorphous metal wires 4 having a diameter of 125 μm were used. This FRP member F is referred to as an example FRP member F.

Figure 15:
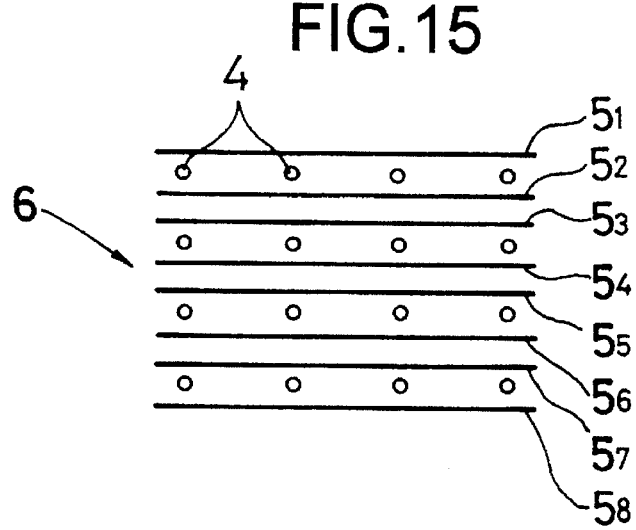
FIG. 15 is a diagram illustrating another example of the relationship between carbon fiber cloths and amorphous metal wires in the FRP member.

As a comparative example 1, as shown in FIG. 15, a plurality of amorphous metal wires 4 similar to those of the previous Example 1 were arranged parallel to each other at a pitch of 0.6 mm at locations between first and second cloths $5_1$ and $5_2$, between third and fourth cloths $5_3$ and $5_4$, between fifth and sixth cloths $5_5$ and $5_6$, and between seventh and eighth cloths $5_7$ and $5_8$, respectively, thereby fabricating an FRP member in the same manner as in Example 1. In this FRP member, the plurality of amorphous metal wires 4 were embedded to form two layers on each side of the surfaces $s_1$ and $s_2$.

Figure 16:
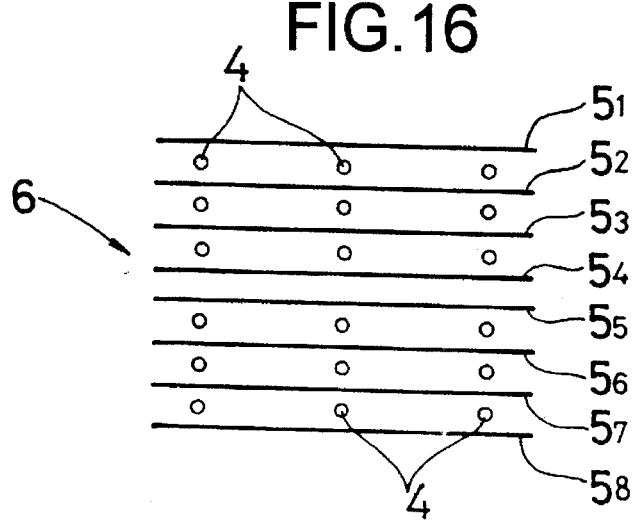
FIG. 16 is a diagram illustrating a further example of the relationship between carbon fiber cloths and amorphous metal wires in the FRP member.

As a comparative example 2, as shown in FIG. 16, a plurality of amorphous metal wires 4 were arranged parallel to each other at a pitch of 0.9 mm at locations between first and second cloths $5_1$ and $5_2$, between second and third cloths $5_2$ and $5_3$, between third and fourth cloths $5_3$ and $5_4$, between fifth and sixth cloths $5_5$ and $5_6$, between sixth and seventh cloths $5_6$ and $5_7$ and between seventh and eighth cloths $5_7$ and $5_8$, respectively, thereby fabricating an FRP member in the same manner. In this FRP member, the plurality of amorphous metal wires 4 were embedded to form three layers on each side of the surfaces $s_1$ and $s_2$.

First, the example FRP member F and the amorphous metal wires 4 of the comparative examples 1 and 2 were subjected to a stress measurement using the stress measuring device $8_1$ shown in FIG. 8. In measuring the stress of the amorphous metal wires 4, end faces of legs 9a of a core 9 were placed against the one surface $s_1$ of the FRP member F, and the oscillator 1 was operated under oscillation conditions where a frequency of a sine wave including no D.C. magnetic field component is 1 kHz and a voltage between peaks, namely, a voltage between peaks in one period is 15 $V_{p—p}$, thereby applying an A.C. magnetic field H exceeding a coercive force Hc of the amorphous metal wire 4 to the exciting coil 2. This caused a magnetic path to be generated between the core 9 and the amorphous metal wires 4, whereby an A.C. electromotive force $V_2$ was induced in the detecting coil 3. This A.C. electromotive force $V_2$ was inputted to the spectral analyzer 10 and then, an effective value Ev1 of third, fifth, seventh and ninth harmonic wave components which were higher harmonic wave components, i.e., a value determined according to the following expression (6), i.e., $Ev1=\sqrt{E_3^2+E_5^2+E_7^2+E_9^2}$, was outputted and determined as a measurement amount of the stress of the amorphous metal wires 4.

Then, the example FRP member F and the like were subjected to a tension-tensile fatigue test to measure a stress of the amorphous metal wires 4 at every predetermined number of repetitions of the stress cycle. Conditions for this fatigue test are a minimum tensile strain of $800 \times 10^{-6}$, a maximum tensile strain of $8,000 \times 10^{-6}$, and a repetition frequency of 20 Hz.

Figure 17:
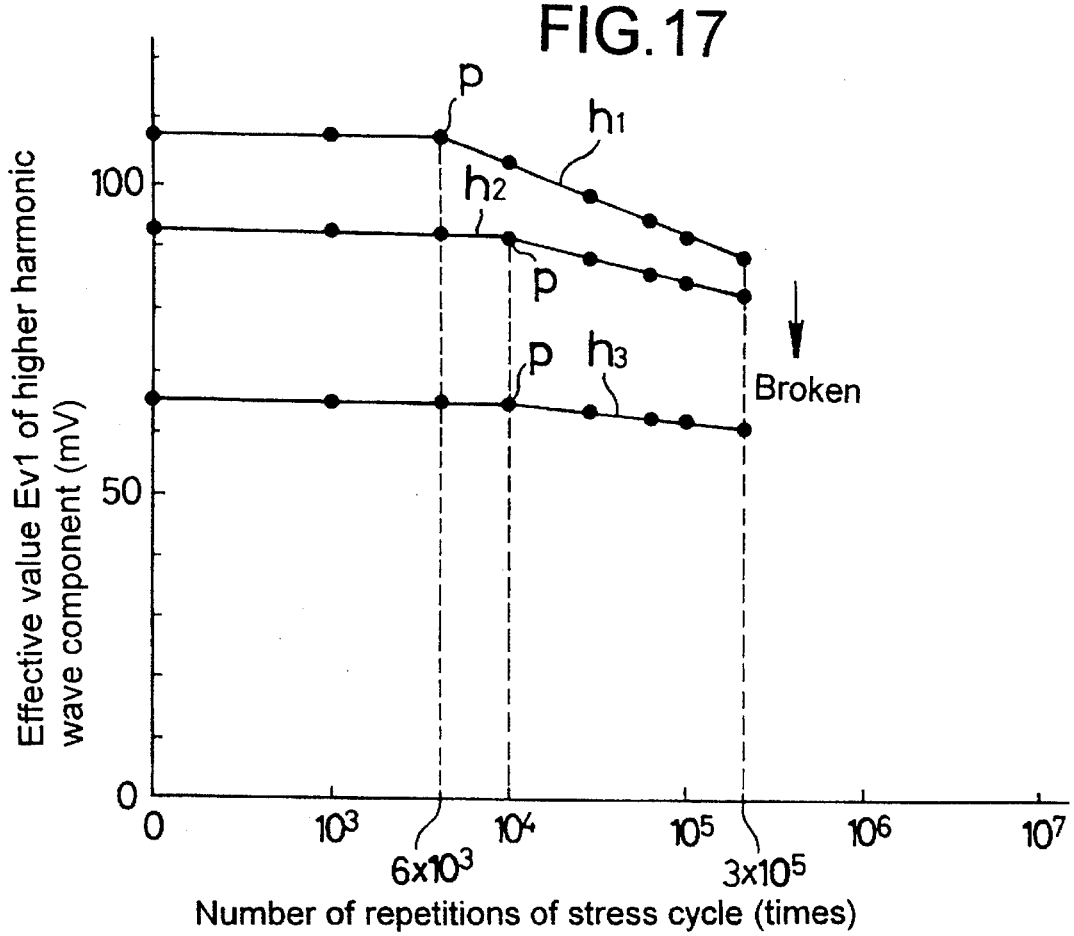
FIG. 17 is a graph illustrating the relationship between the number of repetitions of the stress cycle and the effective value Ev1 of higher harmonic wave components.

A relationship between the number of repetitions of the stress cycle and the effective value Ev1 was examined to provide results shown by lines $h_1$ to $h_3$ in FIG. 17, wherein the line $h_1$ corresponds to the example FRP member F, the line $h_2$ corresponds to the comparative example 1, and the line $h_3$ corresponds to the comparative example 2.

In the example FRP member F shown by the line $h_1$ in FIG. 17, the effective value Ev1 is constant until the number of repetitions of the stress cycle reaches $6 \times 10^3$. It can be found from this that the FRP member F was not damaged. If the number of repetitions of the stress cycle exceeds $6 \times 10^3$, the effective value Ev1 starts lowering. This is because hair cracks, an interfacial separation and/or the like are produced within the FRP member F and hence, the binding force on the amorphous metal wire 4 is reduced and due to this, the stress of the amorphous metal wires is reduced, and the suppression of the magnetostriction oscillation phenomenon under the A.C. magnetic field is moderated. In this case, because a lowering start point p of the effective value Ev1 is extremely distinct, it can be certainly determined that an internal damage was produced in the FRP member F.

In the comparative examples 1 and 2 shown by the lines $h_2$ and $h_3$, the output when the FRP member was not damaged, is lower. As a result, the lowering start point p is located at a position corresponding to $10^4$ times repetitions of the stress cycle. But this point p is unclear, and the sensitivity of detection of the internal damage is remarkably low, as compared with the example FRP member.

EXAMPLE 3

Figure 18:
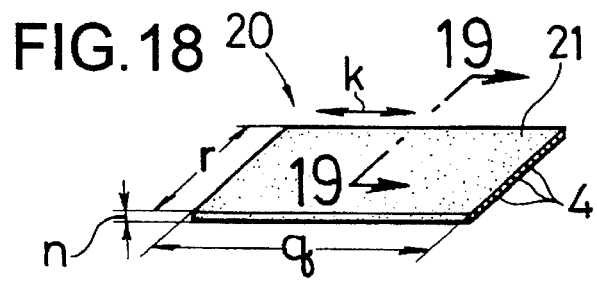
FIG. 18 is a perspective view of an adhesive member.
Figure 19:
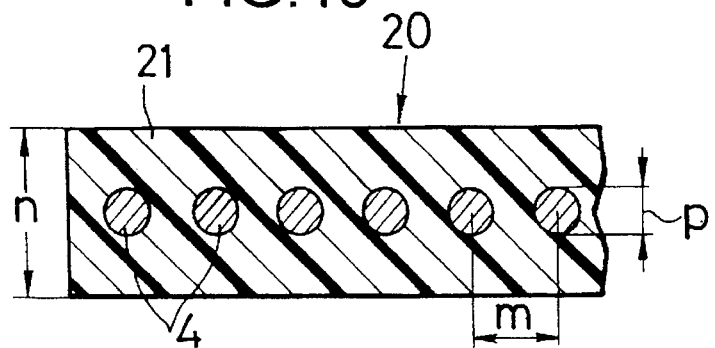
FIG. 19 is an enlarged sectional view taken along a line 19—19 in FIG. 18.

In FIGS. 18 and 19, an adhesive layer forming adhesive member 20 whose internal defection can be detected is in the form of a rectangular and uniform-thickness film and includes a main body 21 formed of uncured adhesive, and a plurality of soft magnetic materials 4 embedded within the main body 21.

As the adhesive for forming the main body 21, a thermosetting synthetic resin adhesive may primarily be used. Examples of such a thermosetting synthetic resin adhesive are a phenolic resin-based adhesive, an epoxy resin-based adhesive, a phenolic epoxy resin-based adhesive and the like, from a viewpoint that they are easily formed into a film. Further, a thermoplastic synthetic resin adhesive may be used.

The soft magnetic material 4 is fibrous, and formed from an amorphous metal in this example. The plurality of soft magnetic materials 4 is arranged at a given pitch m in parallel to a lengthwise direction k of the main body 21.

The thickness n of the adhesive member 20 is suitable to be in a range of $0.03 \text{ mm} \leq n \leq 1.0 \text{ mm}$, and the diameter p of the fibrous soft magnetic material 4 is suitable to be in a range of $30 \text{ μm} \leq p \leq 200 \text{ μm}$. On the basis of these respects, the pitch m of the fibrous soft magnetic material 4 with respect to the diameter p is set in a range of $2p \leq m \leq 10p$.

If the pitch m is set in the above range, the amount of the main body 21 and thus the amount of the adhesive is appropriate and hence a sufficient bonding strength can be obtained. In addition, the distribution state of the fibrous soft magnetic materials 4 is appropriate and hence the stress detecting sensitivity thereof becomes good. However, if m<2p, the volume fraction Vf of the fibrous soft magnetic materials 4 in the adhesive layer is nearly equal to 40% from the relationship to the thickness n. For this reason, the bonding strength becomes insufficient, and during bonding, the fibrous soft magnetic materials 4 are easily intertwined and hence it is difficult to uniformize the thickness of the adhesive layer. On the other hand, if m>10p, the distribution state of the fibrous soft magnetic materials 4 is dispersed, which deteriorates a stress-detecting sensitivity.

Table 1 shows the dimensions and the like for an embodiment of the adhesive member 20. In Table 1, the volume fraction Vf of the fibrous soft magnetic materials 4 shows a value in the adhesive member 20.

TABLE 1

| | |
|---|---|
| Dimension of the adhesive member 20 | In FIG. 18, length q is 40 mm, width r is 25 mm, and thickness n is 0.5 mm |
| Main Body 21 | Material: Epoxy resin-based adhesive (made by 3 M Corp. under a trade name of AF-191) |
| Fibrous soft magnetic material 4 | Material: Amorphous alloy of $Fe_{77.5}Si_{7.5}Bi_{15}$ (each of numerical values is atom %) Coercive force Hc: 0.4 oersted Thermal expansion coefficient: $7.3 \times 10^{-6}/°C$. Diameter p: 125 μm Pitch m: 0.3 mm (Vf = 8%) |

Figure 20:
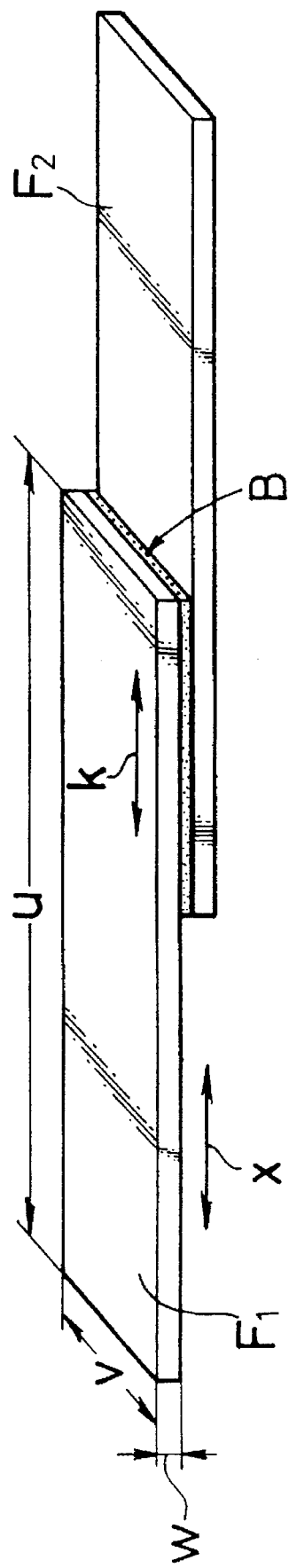
FIG. 20 is a perspective view of two FRP members bonded to each other through an adhesive layer.

As shown in FIG. 20, two plate-like FRP members $F_1$ and $F_2$ having the same structure and the same dimension were prepared as members to be bonded. In these FRP members F and $F_2$, a reinforcing fiber member is formrd as a laminate produced by laminating eight cloths made of a carbon fiber having a diameter of 6 μm, so that the orientations of the carbon fibers in the adjacent cloths are offset by 45°. A matrix is formed of epoxy resin. Each of the FRP members $F_1$ and $F_2$ has a length u of 155 mm, a width v of 25 mm, a thickness w of 1.6 mm and a thermal expansion coefficient of $3.5 \times 10^{-6}/°C$.

In bonding both the FRP members $F_1$ and $F_2$ to each other, the entire adhesive member 20 was clamped between one end of the FRP members $F_1$ and $F_2$ with its lengthwise direction k matched with the lengthwise directions of the FRP members $F_1$ and $F_2$. Then, the adhesive member 20 was cured at 180° C. for 1 hour at 3.2 atmospheres. This formed an adhesive layer B, whereby the FRP members $F_1$ and $F_2$ were bonded to each other through this adhesive layer B. At this time, the bonding margin was 10 cm².

In this case, because the thermal expansion coefficient of the fibrous soft magnetic material 4 is 7.3×10⁻⁶/°C. and the thermal expansion coefficient of the FRP members $F_1$ and $F_2$ is 3.5×10–6/°C., the fibrous soft magnetic materials 4 are bound to their tension load-applied state at ambient temperature after curing of the main body 21 by heating and thus after formation of the adhesive layer B.

In measuring the stress, the stress measuring device $8_1$ shown in FIG. 8 is used. However, the detecting coil 3 is wound 140 turns/15 mm around the connecting portion 9b, and the exciting coil 2 is wound 140 turns/15 mm around the outer periphery of the detecting coil 3.

Figure 21:
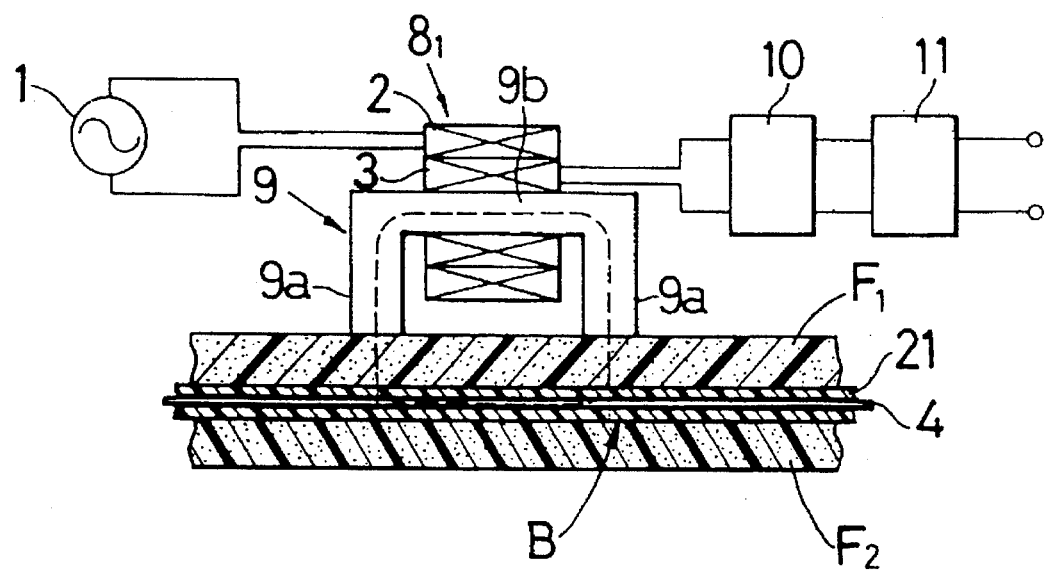
FIG. 21 is a schematic view illustrating a third example of a stress measuring device and a stress measuring process.

First, the fibrous soft magnetic materials 4 in the adhesive layer B were subjected to a stress measurement. In measuring the stress of the soft magnetic materials 4, as shown in FIG. 21, the end faces of the legs 9a of the core were placed against one surface of the FRP member $F_1$, and the oscillator 1 was operated under oscillation conditions where the frequency of a sine wave including no D.C. magnetic field component is 1 kHz and the voltage between peaks is 30 $V_{p-p}$, thereby applying an A.C. magnetic field H exceeding a coercive force Hc of the fibrous soft magnetic materials 4 to the exciting coil 2. This caused a magnetic path to be generated between the core 9 and the soft magnetic materials 4, whereby an A.C. electromotive force $V_2$ was induced in the detecting coil 3. This A.C. electromotive force $V_2$ was inputted to the spectral analyzer 10 and then, a distortion factor K, i.e., a value determined according to the expression (7), i.e., $$K = \frac{\sqrt{E_3^2 + E_5^2 + E_7^2 + E_9^2}}{E_1},$$

was outputted by the calculator 11 and determined as a measurement amount of the stress of the fibrous soft magnetic materials 4. If the soft magnetic materials 4 are magnetized in the above-described manner, a so-called magnetostriction phenomenon producing an elongation in the soft magnetic materials 4 is generated. But the magnetostriction oscillation phenomenon under an A.C. magnetic field is suppressed by the cured main body 21.

Then, outer ends of the FRP members $F_1$ and $F_2$ were clamped by chucks, and a tension-tensile fatigue test was conducted for the adhesive layer B, until it was broken. During that time, the stress of the fibrous soft magnetic materials 4 was measured at every predetermined number of repetitions of the stress cycle. Conditions for this fatigue test are as follows: a distance between the chucks is 150 mm, a minimum tension load is 0.14 tons, a maximum tension load is 1.4 tons, and a repetition frequency is 20 Hz.

Figure 22:
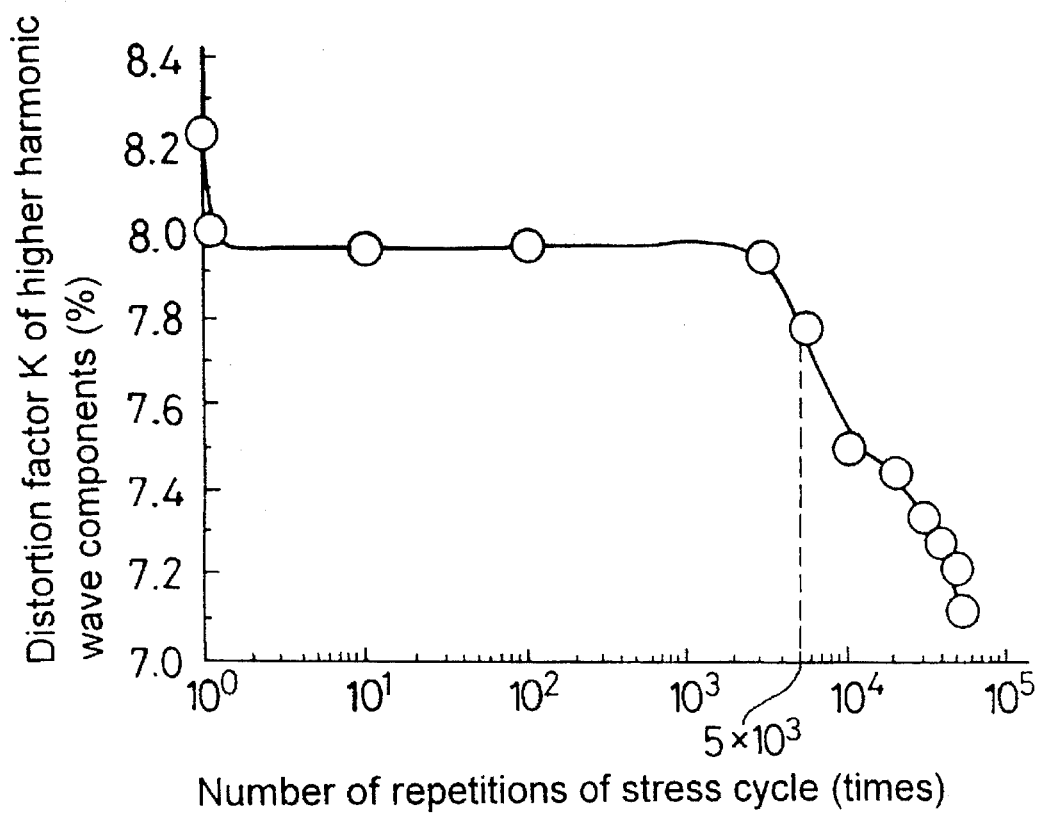
FIG. 22 is a graph illustrating one example of the relationship between the number of repetitions of the stress cycle and the distortion factor K of higher harmonic wave components.

A relationship between the number of repetitions of the stress cycle and the distortion factor K of higher harmonic wave components was found as shown in FIG. 22. The distortion factor K is lowered immediately after the start of the test because the main body 21 is plastically deformed. However, thereafter, the distortion factor K is constant, until the number of repetitions of the stress cycle reaches 2×10³, and it can be found from this that the adhesive layer B is not damaged. If the number of repetitions of the stress cycle exceeds 2×10³, the distortion factor K starts lowering. This is because a damage was produced within the adhesive layer B and hence, the binding force on the fibrous soft magnetic materials 4 was reduced and due to this, the stress of the soft magnetic materials 4 was reduced, and the suppression of the magnetostriction oscillation phenomenon under the A.C. magnetic field was moderated. At the number of repetitions of the stress cycle of 5×10³, the section of the adhesive layer B was observed by a microscope and it is was confirmed that cracks were produced.

Figure 23:
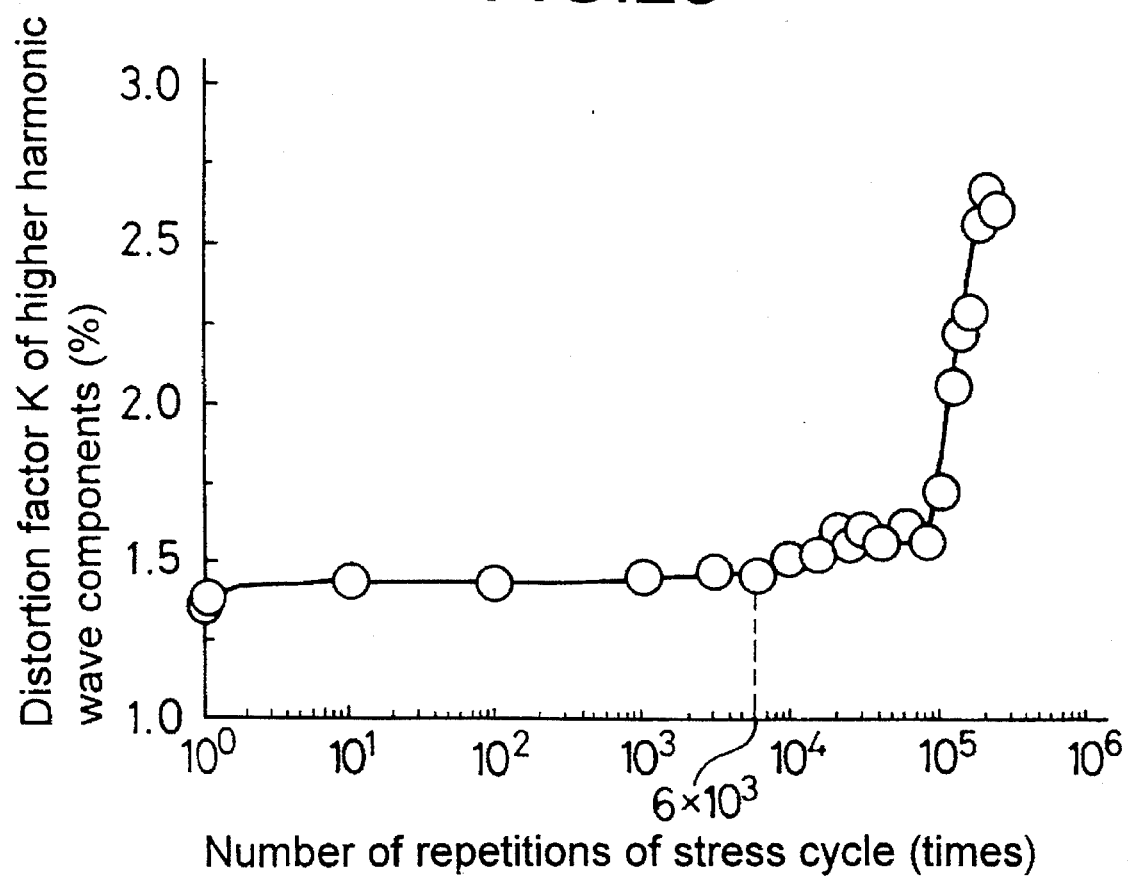
FIG. 23 is a graph illustrating another example of the relationship between the number of repetitions of the stress cycle and the distortion factor K of higher harmonic wave components.

FIG. 23 illustrates another tension-tensile fatigue test example. A test piece used in this test example was produced by bonding any one of the FRP members (in this test, FRP member $F_1$ was used) to a steel plate (JIS 45C having a length u of 155 mm, a width v of 25 mm, a thickness w of 4 mm and a thermal expansion coefficient of 11.2×10⁻⁶/°C. using the above-described adhesive member 20 in the same manner as that described above. In this case, the fibrous soft magnetic materials 4 are bound to their tensile load-applied states due to the fact that the thermal expansion coefficient of the steel plate is larger than that of the FRP member $F_1$.

Conditions for this test were the same as those for the above-described test, except that the minimum tensile load was set at 0.06 tons and the maximum tensile load was set at 0.55 tons. In order to enhance the sensitivity, the core 9 of the stress measuring device 8 was disposed on the side of the FRP member $F_1$.

In FIG. 23, the distortion factor K is slightly increased because the main body 21 is plastically deformed immediately after the start of the test. However, the distortion factor K thereafter becomes constant until the number of repetitions of the stress cycle reaches 6×10³, and it can be found from this that the adhesive layer B is not damaged. Then, when the number of repetitions of the stress cycle exceeds 6×10³, the distortion factor K starts increasing. This is because the interior of the adhesive layer was damaged, thereby lowering the binding force on the fibrous soft magnetic materials 4 and due to this, the stress of the soft magnetic materials 4 was lowered, and the suppression of the magnetostriction oscillation phenomenon under the A.C. magnetic field was moderated. At the number of repetitions of the stress cycle of 10⁴, the section of the adhesive layer B was observed and it was confirmed that cracks were produced between the fibrous soft magnetic materials 4 and the cured main body 21.

A glass fiber may be contained in the adhesive member 20 in order to reinforce the latter. The adhesive member may be formed from metal, or another material such as wood, ceramics and the like.

The stress measurement amount of the soft magnetic material is not limited to the distortion factor K, and an effective value of one or more higher harmonic wave components, a voltage between peaks, a crest value or the like may be used as the stress measurement amount.

What is claimed is:

1. An adhesive member for forming an adhesive layer for bonding a first member and a second member to each other to provide an integrated article, and for defecting an internal defection in said adhesive layer by utilizing a magneto-mechanical property of a soft magnetic material, said adhesive member comprising a main body formed of an uncured adhesive and a plurality of soft magnetic materials embedded in said uncured adhesive of said main body, said soft magnetic materials being held in a state subjected to an external force after curing of said main body.

2. An adhesive member for forming an adhesive layer according to claim 1, wherein said soft magnetic materials are fibrous and arranged parallel to each other at given distances therebetween within said main body.

3. An adhesive member for forming an adhesive layer according to claim 1 or 2, wherein said soft magnetic materials are formed of an amorphous metal.

* * * * *

UNITED STATES PATENT AND TRADEMARK OFFICE
CERTIFICATE OF CORRECTION

PATENT NO. : 5,640,088
DATED : June 17, 1997
INVENTOR(S) : Sasahara et al.

It is certified that error appears in the above-identified patent and that said Letters Patent is hereby corrected as shown below:

Title page,
Under Item "[73] assignee, correct the spelling of the Assignee by deleting "Kabushki" and substitute -- Kabushiki --.

Column 14,
Line 51, after "and for" delete "defecting" and insert -- detecting --.

Signed and Sealed this

Seventh Day of May, 2002

*Attest:*

JAMES E. ROGAN
*Attesting Officer*    *Director of the United States Patent and Trademark Office*